United States Patent [19]

Skov et al.

[11] Patent Number: 4,869,875
[45] Date of Patent: Sep. 26, 1989

[54] METHOD OF DETECTING OR DETERMINING HISTAMINE IN HISTAMINE CONTAINING MATERIALS, PARTICULARLY BODY FLUIDS AND AN ANALYTICAL AGENT FOR USE IN SUCH METHOD

[76] Inventors: Per S. Skov, Kanslergade 6 st., 2100 Copenhagen Ø; Svend Norn, Skovvang 1, 3460 Birkerød; Bent Weeke, Tølløsevej 20, 2700 Brønshøj, all of Denmark

[21] Appl. No.: 791,722

[22] Filed: Oct. 28, 1985

Related U.S. Application Data

[62] Division of Ser. No. 300,262, Sep. 8, 1981, Pat. No. 4,550,085.

[30] Foreign Application Priority Data

Jul. 6, 1981 [DK] Denmark ............................ 81-2982

[51] Int. Cl.⁴ ............................................. G01N 31/22
[52] U.S. Cl. ...................................... 422/58; 422/61; 435/7; 436/527; 436/541; 436/169; 436/177; 436/808; 436/810; 436/811
[58] Field of Search ............... 436/177, 178, 170, 169, 436/807, 810, 527, 811, 541, 804; 210/767, 509, 500.1, 782, 927, 503, 505, 508; 422/55–58, 61, 73; 435/7

[56] References Cited

U.S. PATENT DOCUMENTS

| | | | |
|---|---|---|---|
| 3,941,876 | 3/1976 | Marinkovich | 436/810 X |
| 4,235,601 | 11/1980 | Deutsch et al. | 422/71 X |
| 4,256,693 | 3/1981 | Kond et al. | 422/56 |
| 4,299,813 | 11/1981 | Snyder | 422/61 X |
| 4,331,650 | 5/1982 | Brewer et al. | 422/56 X |
| 4,477,575 | 10/1984 | Vogel et al. | 422/56 X |
| 4,579,828 | 4/1986 | Ali | 422/73 X |
| 4,629,706 | 12/1986 | Hammond et al. | 422/73 X |

FOREIGN PATENT DOCUMENTS 2244080  3/1973  Fed. Rep. of Germany ...... 436/807

OTHER PUBLICATIONS

Goodman et al., *The Pharmacological Basis of Therapeutics*, 6th Ed., MacMillan Publishing, NY, pp. 608–633.
"Receptor Site Analysis", New England Nuclear Product Brochure, Oct. 1979.
Averso, American Laboratory, vol. 8, No. 4, pp. 97–98, 101, 102, 104.

*Primary Examiner*—Barry S. Richman
*Assistant Examiner*—Jill Johnston
*Attorney, Agent, or Firm*—Darby & Darby

[57] ABSTRACT

Histamine is detected or determined selectively in a sample by causing the sample to contact glass microfibers in such a quantitative proportion as will permit the present histamine to bind to the fibers. The fiber bound amount of histamine may be determined by competitive determination in the presence of labelled histamine on the basis of a standard curve, or may be determined directly by conventional coupling reactions. The method is simple and particularly useful for allergy diagnostics because it exhibits good correlation with known fluorometric methods.

16 Claims, 5 Drawing Sheets

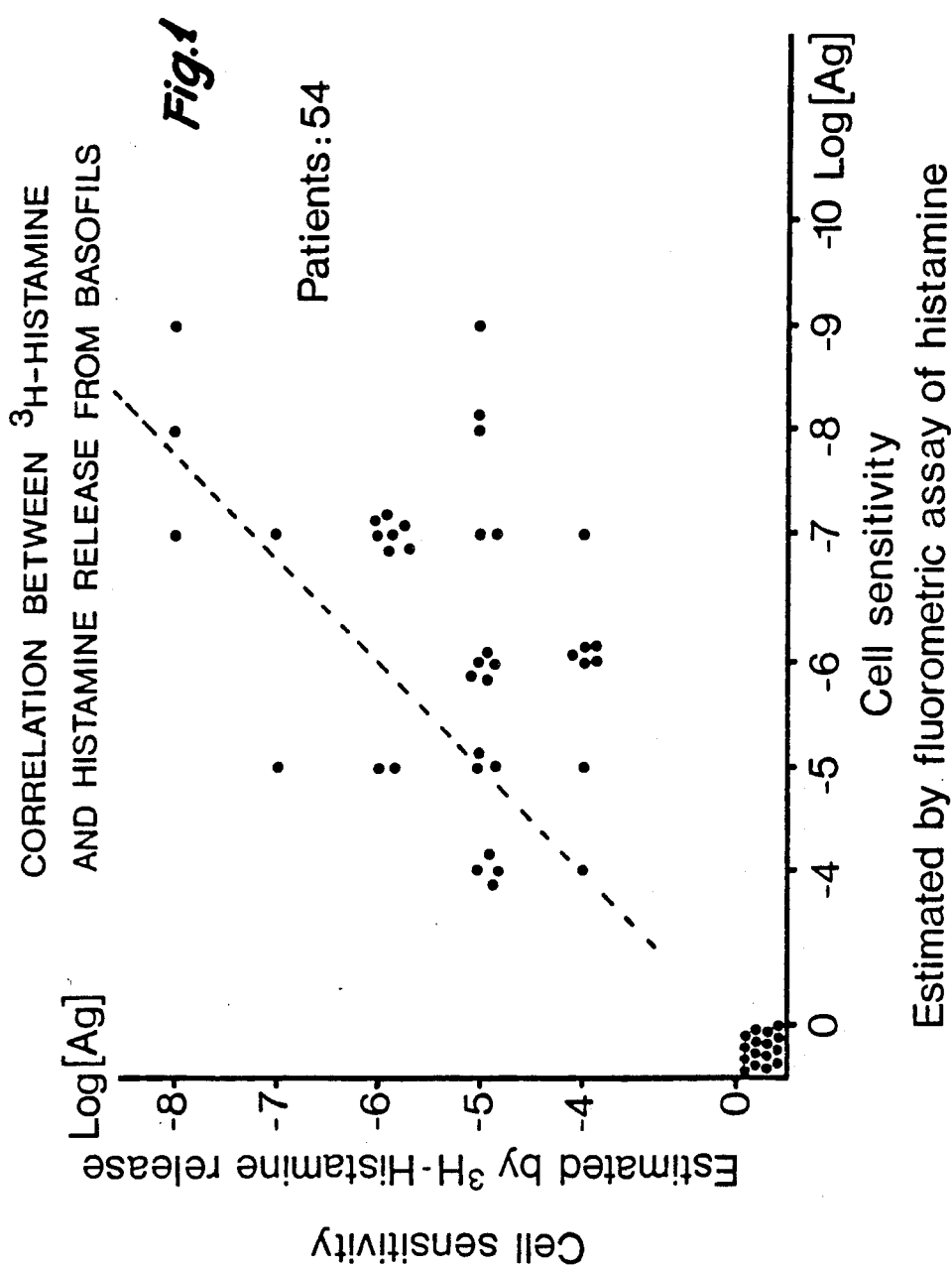

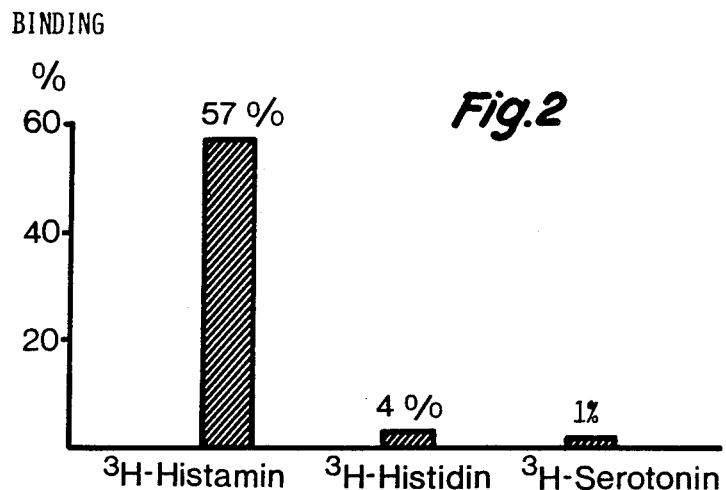

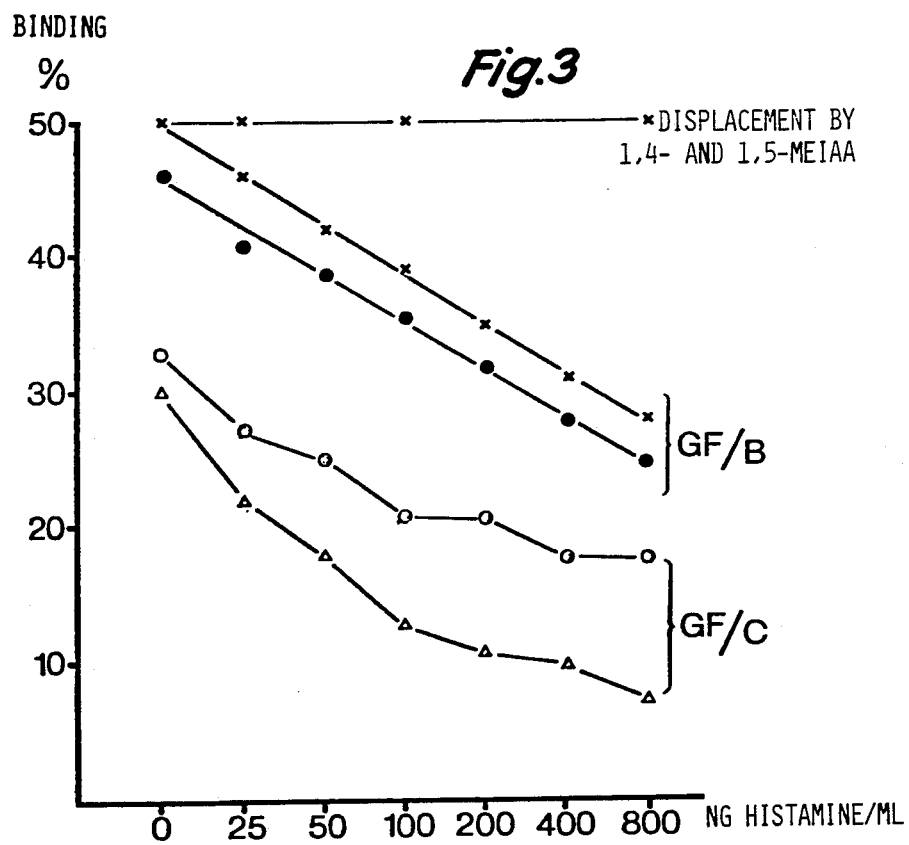

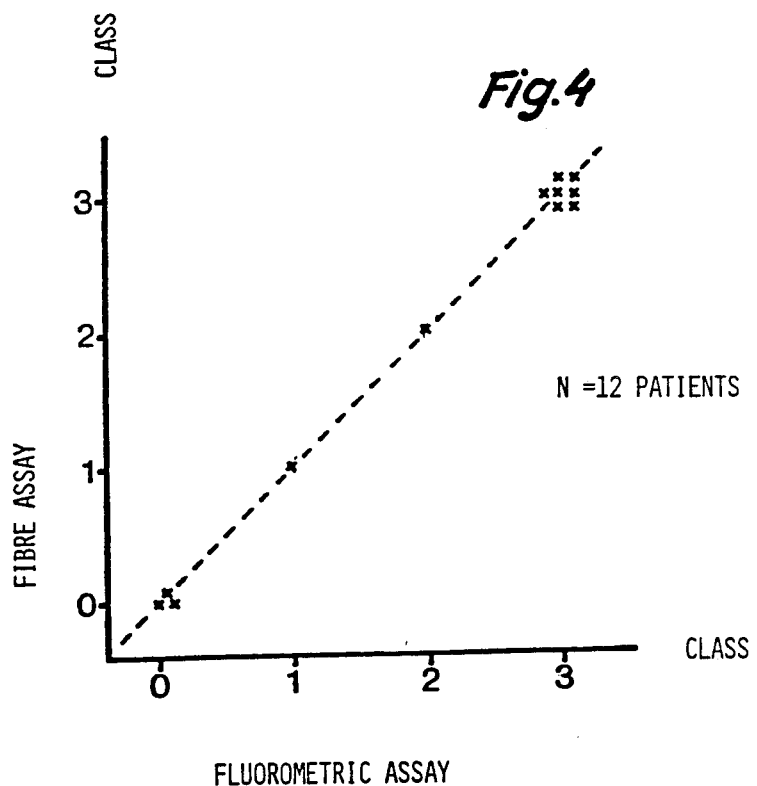

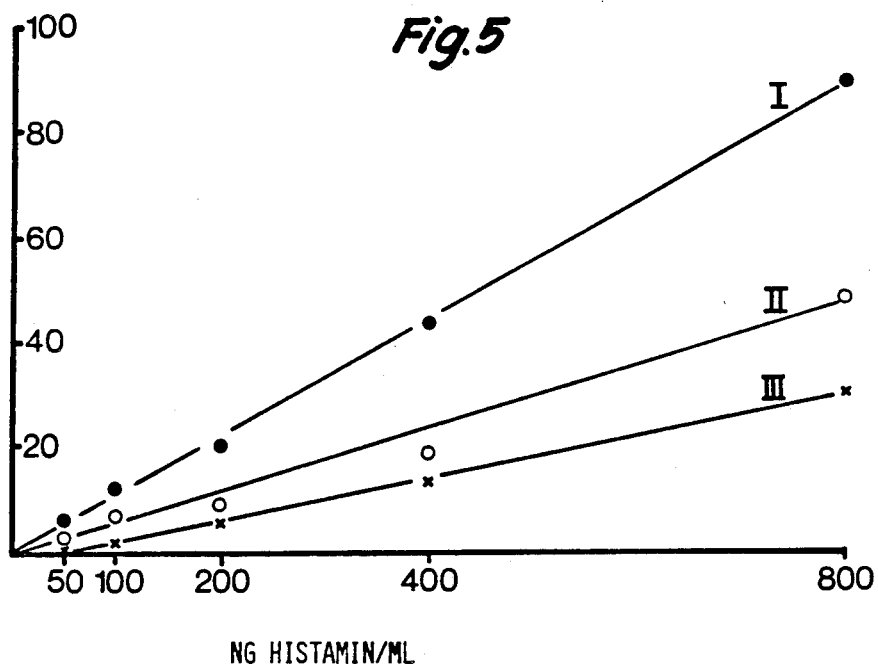

METHOD OF DETECTING OR DETERMINING HISTAMINE IN HISTAMINE CONTAINING MATERIALS, PARTICULARLY BODY FLUIDS AND AN ANALYTICAL AGENT FOR USE IN SUCH METHOD

This is a division of application Ser. No. 300,262, filed 9/8/81, now U.S. Pat. No. 4,550,085.

The present invention relates to a method of detecting or determining histamine in histamine-containing materials, particularly blood or blood fractions. The invention also relates to an analytical agent to be used in the performance of the method.

One of the problems in the treatment of allergic diseases is the lack of diagnostic techniques which are sufficiently specific and sensitive and which do not imply any risk to the patient. Furthermore, there is a need for a rapid, simple, and inexpensive diagnostic technique which would ensure a decrease in the number of patients now waiting for adequate treatment.

In human blood and tissue there exist specific cells (basophil leucocytes and mast cells) which are involved in the allergic reaction. On the surface of these cells is a distinct class of antibodies (IgE-antibodies). When e.g. a patient is allergic to cat, this allergic reaction is caused by the antibodies on the surface of these cells which specifically recognize the protein structure of cat dandruff. When inhaled, cat protein gets in contact with the mast cells and the basophil leucocytes of the lung tissue. The antibodies on the cell surface will react with cat protein, hereby triggering a reaction in the cell, which in turn causes the release of a number of substances (allergic mediators). These allergic mediators are responsible for the symptoms of the patient.

For many years it has been possible to imitate the allergic reaction (in vitro). This is done by taking a blood sample from the allergic patient. By exposing the blood sample to e.g. cat protein, the allergic mediators will be released from the basophil leucocytes in the blood sample. Of these mediators it has been possible to determine one substance, i.e. histamine. Therefore, if the patient is allergic to cat, it is possible to determine the release of histamine from the cells. Methods based on this principle represent the best assay for obtaining a correct diagnosis, and are explained in detail below.

By means of this technique it is possible to diagnose the responsible antigens (e.g. grass pollen, animal dandruff, drugs, foodstuffs, mould fungi, and bacteria) in patients with allergic diseases (asthma, urticaria, and hay fever).

A general problem of this test is that it is difficult to perform in the laboratory. Here only few tests can be performed daily and the demand for laboratory technicians is high. Therefore, a simplification of the test is greatly needed so that it could be introduced in the daily diagnostic routine of the clinic.

As mentioned, there exists a number of assays for detecting histamine in liquids. Thus, the original histamine determination was described by Shore et al. and was based on a fluorometric assay (ref. 1).

The principle of this assay is a coupling of histamine to a fluorophore (o-phthalaldehyde), whereby a ring structure is formed. The amount of this ring structure, which can be determined spectrophotometrically, depends on the amount of histamine. The method has later been modified to increase specificity and sensitivity. Stahl Skov & Norn (ref. 2) have thus simplified the assay by allergen-provocation of Ficoll-Hypaque-isolated cell suspensions containing ½-2% basophil leucocytes instead of whole blood. By fractionation of the blood, interfering substances are removed, so that the histamine content of the basophil leucocytes can be determined directly, avoiding a long extraction procedure. However, the fractionation procedures (gradient centrifugation) necessary to remove interfering substances are time consuming and difficult to perform, and Siraganian therefore developed an autoanalytical fluorometric method (ref. 3). This method is used in the clinic, but has only found limited application, due to its demand for technical experience, constant monitoring, and expensive apparatus.

Taylor et al. (ref. 4) has developed another assay for determining histamine in biological material. This very sensitive and specific method is an enzymatic isotope technique based on methylation of histamine by means of N-methyltransferase. It has thus been possible to determine small amounts of histamine in tissue, blood, and urine. However, the need for a routine method to be used in the clinic is not satisfied by this method since the number of assays per day is low (approx. 30) and the assay time is long.

Stahl Skov et al. (ref. 5) has developed another method based on in vitro incorporation of radioactively labelled histamine in the basophil cells of the patient, where the release of labelled histamine is determined after provocation with the suspected allergens.

However, as illustrated below, a poor correlation with the release of histamine determined fluorometrically was obtained by this method.

The purpose of the present invention is to provide a method for the detection or determination of histamine, which is not vitiated by the drawbacks of the known methods such as apparatus requirements, time consumption, and pretreatment of the blood samples.

In particular, it is the purpose of the invention to provide a simple and more specific method for the detection and determination of histamine in histamine-containing materials, which is rapid and easy to perform, which only requires a small amount of material, and which does not make heavy demands on the training of the staff.

This is achieved by the method of the invention, which comprises: contacting a sample of the material with glass microfibres in such quantitative proportions between the glass microfibres and the material as will permit the histamine amount to be detected or determined or to be bound to the microfibres; and registering or measuring the bound amount of histamine. As mentioned, the invention also relates to an agent for use in the performance of the method, and this agent is characterized by comprising glass microfibres deposited into a carrier.

The invention is based on the surprising finding that histamine is selectively bound to glass microfibres even after repeated washings. Glass microfibres are extensively used as filters and described in detail, e.g. in the brochure "Glass Microfibre Filters", Publication No. 630, Whatman, Springfield Mill, Maidstone, Kent, England, which is incorporated by reference. In this brochure it is emphasized that they exhibit extremely low adsorption capacity, but have in a few cases been used as a means to adsorb high molecular substances, especially proteins, such as albumin and poly U in RNA assays.

The binding of histamine to the glass microfibres is surprising because histamine does not bind to cellulose fibres, dextran gels of the "Sephadex®", type or aluminium hydroxide gels whose high adsorption capacity is well-known.

The binding is even more surprising because low molecular compounds such as serotonin and histidine as well as the histamine metabolites 1,4- and 1,5-methyl imidazole acetic acid do not bind to the fibres, which is demonstrated below.

Glass microfibers are commercially available and are non-toxic and not dangerous to use. A glass microfibre filter marketed under the trade mark "Whatman®GF/B" has been found very suitable for the carrying out of the present method. Also the type "Whatman®GF/C" may be used, but has more varying binding properties.

It appears from the above-mentioned brochure that the said fibres are boron silicate fibres with the following typical oxide content:

|        | %    |     | %   |
|--------|------|-----|-----|
| $SiO_2$ | 57.9 | CaO | 2.6 |
| $B_2O_3$ | 10.7 | MgO | 0.4 |
| $Fe_2O_3$ | 5.9 | BaO | 5.0 |
| $Al_2O_3$ | } 10.1 | ZnO | 3.9 |
| $Na_2O$ | | F | 0.6 |
| $K_2O$ | 2.9 |     |     |

The invention is of course not restricted to the use of glass microfibres of the above-mentioned types, and the skilled person will be able to find fibres of optimal binding properties among the commercially available glass fibre types by simple binding tests, as described below in example 1.

However, it is assumed at present that the most suitable glass microfibres are those of the type "Whatman GF/B" and fibres of similar properties, particularly binding properties. To obtain the desired sensitivity, the glass microfibres are advantageously divided into fine particles as small as 2 to 20 μm, before they are used in the method of the invention. Here too the most appropriate fibre dimension and disintegration degree can be determined by tests and also depend on the carrier onto which the fibres are to be deposited to provide the most expedient assay, according to the material in which a possible content of histamine is to be determined or detected.

The quantitative proportion between the glass microfibres and the histamine-containing material can likewise be determined by tests depending upon the expected amount of histamine to be bound to the fibres. The amount of histamine released at various degrees of allergy is well-known from the literature, so that standard curves for predetermined histamine amounts may be plotted and serve as a basis for determination of the amount of histamine in an unknown sample, e.g. by a competitive determination, as explained in detail below.

A suitable carrier type is tubes of glass or particularly plastic in the form of a small test tube, but also glass plates, foils or strips may be used. For allergy diagnostics, the glass fibres may advantageously be deposited onto suitable carriers together with test allergens and made up into suitable test devices, e.g. in the form of diagnostic kits.

The method of the invention is particularly useful for the detection or determination of histamine released as a consequence of an allergic reaction, in which a blood sample is to be used as the test material. In addition to the general advantages explained in the foregoing, the method provides the significant advantage over the known methods that it is sufficient to remove the blood plasma, e.g. by centrifugation and washing with a physiological buffer. If desired, the red blood cells (erythrocytes) may also be removed, which can be done simply e.g. by sedimentation by addition of dextran.

The method can also be used for detection or determination of histamine in other body fluids from humans and animals, such as lymph, cerebrospinal fluids or urine, or in tissue samples or tissue extracts. In this context it is noted that histamine is released in diseases other than allergies, e.g. mastocytosis.

Finally, the method may be used for detection or determination of histamine in foodstuffs, e.g. fish such as mackerel and the like.

The registration or measurement of the histamine bound to the microfibres may take place on two different principles, viz.

1. Competitive determination including the use of labelled histamine.
2. Direct determination.

1. Competitive determination

This principle of registration is based on a competition for the binding sites on the glass microfibres between histamine possibly present in the sample and a predetermined amount of added labelled histamine.

When plotting a standard curve fior varying known concentrations of unlabelled histamine together with a given amount of labelled histamine, it is easy to determine the amount of histamine in a specific sample by adding the amount of labelled histamine used for the standard curve. This is explained more fully below in Example 1 with reference to FIG. 3.

In the following Examples 1 and 2 a radioactive isotope ($^3$H-tritium) is used for the labelling of histamine, but also other radioactive isotopes may be used, such as $^{125}$I. The bound amount of radioactively labelled histamine may easily be determined in a manner known per se, e.g. with a scintillation detection counter.

Due to the difficulty in handling radioactive materials, many new test systems have been developed in the allergy diagnostics which comprise the use of materials other than radioactive isotopes as labelling agents. Examples of this are free radicals, fluorescent molecules (e.g. fluorescein isothiocyanate and rhodamine colouring substances), luminiscent molecules, bacteriophages, enzymes, coenzymes, and enzyme inhibitors.

It generally applies that the labelling agent is not critical, provided that the binding properties of the histamine to the fibres are not affected in a non-reproducible manner, and can be imparted to the histamine according to methods known per se. The crux of the method of the invention is the finding that histamine surprisingly binds selectively to the glass microfibres. When it has been realized in the light of this that a competitive assay is possible and appropriate, it should be a matter of routine for the skilled person to test the conventional labelling methods to find the most suitable methods for the assay in question. At present the use of isotope-labelled histamine in the form of 2,5-$^3$H-histamine dihydrochloride is preferred, because this procedure is rapid and convenient and provides good accuracy and reproducibility.

2. Direct determination

The selective adsorption properties of the glass microfibres make them of course also suitable for direct binding of the histamine present and for subsequent determination of the bound histamine in a conventional manner, e.g. by coupling with a fluorophore compound and subsequent fluorometric measurement. This procedure is illustrated in Example 3 below.

The preparation of plastic tubes containing glass microfibres for use in the present method is easy and inexpensive (5000 to 10,000 tubes per day). The method has proved to be time-saving, as one laboratory technician can prepare about 400 samples per day, as compared with the previous maximum of 150. The method is also blood-saving, as it only requires 10 ml of blood for the determination of 8 to 10 allergies per patient, whereas the known methods require 50 ml of blood.

Since the method is both reproducible and specific and exhibits good correlation with fluorometric histamine determination, it is particularly useful to provide precise information about suspected allergens such as house dust, animal dandruff, pollen, mold fungi, drugs, foodstuffs, bacteria, and autoantigens. The method of the invention is illustrated in detail in the following examples with reference to the drawing, in which FIG. 1 shows a correlation between histamine determinations performed according to Stahl Skov et al. (Ref. 5) and by fluorometric assay, FIG. 2 shows the percentage of binding of tritiated histamine, histidine, and serotonin, respectively, in equimolar concentrations to glass microfibres, FIG. 3 shows the binding of varying concentrations of tritiated histamine to two different glass microfibre types after addition of known amounts of unlabelled histamine and demonstrates the lack of displacement of tritiated histamine caused by the two histamine metabolites 1,4- and 1,5-methyl imidazole acetic acid (MEIAA) and is explained in connection with Example 1, FIG. 4 shows a correlation between histamine determinations performed by the method of the invention and fluorometric assay, and is explained in connection with Example 2, and FIG. 5 shows an adapted direct fluorometric histamine determination by the method of the invention with varying washing procedures compared with conventional determination in the absence of fibres (Ref. 2), and is explained in connection with Example 3.

The measurements in FIG. 1 clearly confirm the lacking correlation between the method of Ref. 5 and the conventional fluorometric determination. The axes show declining concentrations (dilutions) of grass pollen antigen.

It clearly appears from FIG. 2 that histamine is bound surprisingly better than the low molecular compounds histidine and serotonin (5-hydroxy tryptamine). This is also of great importance to the reliability of the histamine determination since, in a number of the known methods, both compounds can interfere with histamine.

It appears from FIG. 3, which is discussed in greater detail below that the two histamine metabolites 1,4-MEIAA and 1,5-MEIAA are not bound either to glass microfibres in the same concentration range as histamine, as they are not able to displace bound labelled histamine from the fibres in a competitive binding assay.

EXAMPLE 1

Preparation of glass fibre prepared tubes

"Whatman GF/B" glass fibre filters are cut into lengths of about ½ mm. 3.4 g are mixed with 500 ml of redistilled water and homogenized for 2 minutes in an "ULTRA TURRAX" blender. The crushed fibres are left for 2 hours at room temperature for sedimentation. The heavy fibres (the longest ones) precipitate, and a supernatant clearly separated from the heavy fibres and containing suspended fibres of dimensions from about 20 $\mu$m to 2 $\mu$m is removed (a total of about 100 ml) and 100 $\mu$l of this supernatant are transferred to plastic tubes. The tubes are dried in an oven at 150° C. (for 1 week), and are then taken out of the oven and are ready for use when the temperature is about 20° C. With this drying procedure the glass fibres are fixed to the bottom of the tubes. The glass fibre-prepared tubes have unlimited shelf life.

Plotting of standard curve for histamine determination

Known dilutions of unlabelled histamine are prepared in Tris-AMC buffer (tris-(hydroxymethyl)-amino methane 25 mM, pH 7.6, NaCl 0.12M, KCl 5 mM, $CaCl_2$ 0.6 mM, $MgCl_2$ 1.1 mM, human serum albumin 0.3 mg/ml and glucose 1 mg/ml). The histamine content was 25 ng, 50 ng, 100 ng, 200 ng, 400 ng and 800 ng/ml, respectively, and the O-sample used was histamine-free buffer. These concentrations are used for the plotting of a standard curve. 100 $\mu$l of these dilutions are transferred to each glass fibre test tube, to which are added 10 $\mu$l of radioactively labelled histamine (2,5-$^3$H-histamine-dihydrochloride: 500 nCi/ml corresponding to 5 nCi/sample, specific activity about 53 Ci/mmole). The samples are incubated for 40 min. at 37° C. To obtain uniform results it is essential to observe the same periods of time for each sample. The samples are washed for 15 sec. with redistilled water in a cell harvester (Tech-Nunc, Roskilde, Denmark). The residual water is discarded, and 1.2 ml of Filter Count (Packard) are added. The samples are counted for 1 min. in a liquid scintillation counter, the emission of the $\beta$-radiation being recorded in counts per minutes (cpm). The sample without unlabelled histamine (O-binding) contains bound labelled histamine in an amount of typically 2000 cpm, which constitutes about 60% of the total amount of labelled histamine added to the sample. The sample containing 25 ng/ml of unlabelled histamine binds to the fibres in an amount corresponding to about 15% of the O-binding and thus gives a count of about 1700 cpm. Increasing amounts of histamine result in an additional decrease in cpm—linearly up to 100 $\mu$g histamine/ml.

The standard curve shown in FIG. 3 with the symbol GF/B for two parallel tests shows a semilogarithmically linear correlation between % binding, expressed as cpm (the y-axis) and histamine content (the y-axis: logarithmic). The sensitivity of the assay is about 25 ng histamine/ml. The figure shows two corresponding tests with fibres of the type "Whatman GF/C" prepared in the same manner, and these fibers exhibit a somewhat poorer correlation.

EXAMPLE 2

Determination of specific allergy to grass pollen in 12 asthmatic patients by in vitro provocation of the basophil leucocytes of the patients with grass pollen.

10 ml of blood are drawn from each patient by venipuncture. The blood is mixed with 0.5 ml of 0.2M EDTA (pH 7.2). The sample is divided into two parts, one of which is analyzed as described in Ref. 2 to demonstrate the correlation between the method of the invention and fluorometric determination. 5 ml of blood are mixed with 1 ml of dextran (molecular weight 500,000 g/mol 45 mg dissolved in 1 ml of 0.9% NaCl) to remove the erythrocytes (the red blood cells). The sample is carefully inverted and left for 30 min. at room temperature. The sedimentation of the erythrocytes is more rapid than that of the leucocytes (the white blood cells). The plasma layer containing the leucocytes is transferred to another tube and suspended in 20 ml of Tris-AMC buffer (cf. Example 1). The leucocyte suspension is centrifuged for 10 min. at 110 g and 16° C. The supernatant is removed and the cells are suspended in 20 ml of Tris-AMC buffer and centrifuged for 10 min. at 60 g and 16° C. The supernatant is again removed, and the cells are resuspended in 5 ml of Tris-AMC buffer. The cell suspension contains 2 to 4% of basophil leucocytes.

100 $\mu$l of the cell suspension are transferred to glass microfibre tubes prepared as in Example 1. 10 $\mu$l of grass pollen are added in a 10-fold dilution series ($10^{-3}$, $10^{-4}$, $10^{-5}$ v/v) of a grass pollen standard preparation and 10 $\mu$l of isotope-labelled (tritiated) histamine are added to the tubes, corresponding to 5 nCi per sample. The samples are incubated for 40 min. at 37° C. The samples are washed for 15 sec. with redistilled water in a cell harvester (Tech-Nunc, Roskilde, Denmark). The residual water is discarded, and 1.2 ml of Filter Count (Packard) are added. The samples are counted in a liquid scintillation counter. In case of allergy to grass pollen, the basophil cells in the sample will release histamine in increasing amounts at increasing grass pollen concentrations. The released histamine is bound to the glass microfibre tubes in competition with the isotope-labelled histamine, and the binding of the isotope-labelled histamine will therefore decrease. A fall in the binding of the isotope-labelled histamine of 10% in relation to a cell sample without grass pollen is considered positive allergy to grass.

The histamine content in the unknown sample may also be calculated by the standard curve discussed in Example 1.

As appears from FIG. 4, an extremely good correlation was found between the histamine release measured by the glass microfibre method and fluorometric determination of histamine, since the investigation of 12 patients showed identical values of the histamine release measured by the two methods. It is noted that the sensitivity of the patient to the allergen is divided into classes where 0 means no reaction, while 3 represents the greatest reaction. Thus, the correlation applies to both non-allergic patients and all three classes of allergy.

EXAMPLE 3

In a modification of the method according to the foregoing Example 2, histamine is determined direct after binding to glass microfibre filters.

Glass microfibre discs: Discs of a diameter of 6 mm are punched out of GF/B filters.

A: 10 $\mu$l of unlabelled histamine dissolved in Tris-AMC buffer, cf. Example 1 (800 ng—400 ng—200 ng—100 ng—50 ng and 0 histamine/ml Tris-AMC), are incubated for 40 min. at 37° C., followed by washing with H$_2$O for 15 sec. in a cell harvester. Residual H$_2$O is removed from the discs. Histamine bound to the discs are determined fluorometrically. Coupling is made with 400 $\mu$l of NaOH/OPT (10 mg o-phthaldialdehyde (Fluka) are dissolved in 5 ml of methanol and mixed with 18 ml of 0.05M) for 4 min. at room temperature. To stabilize the fluorophore 400 $\mu$l 0.175M H$_3$PO$_4$ is added. The samples are centrifuged at 2800 g for 10 min. Reading of the extinction is performed by means of an AMINCO fluorometer (see curve III in FIG. 5).

B. The following control is included: 10 $\mu$l of histamine in the same concentration as used in A are incubated with discs for 40 min. at 37° C. The samples are not washed in a cell harvester, but are immediately coupled as stated in A (see curve II in FIG. 5).

C. The following additional control is included: 10 $\mu$l of histamine in the same concentrations as used in A are incubated for 40 min. at 37° C. in the absence of discs. The samples are not washed in a cell harvester, but are immediately coupled as stated in A (see curve I in FIG. 3).

The three curves thus show:

I: total amount of histamine added to the test tubes.

II: total amount of histamine added to the filter discs in the test tubes.

III: histamine binding to the filter discs after washing.

Although this procedure is not optimized in the above examples, curve III clearly shows the fine linear correlation between the various histamine concentrations and the binding to the fibers.

REFERENCES (all being incorporated by reference)

1. W. Lorenz et al.: A sensitive and specific method for the determination of histamine in human whole blood and plasma. Hoppe-Seyler's Z. Physiol. Chem. 353: 911–920, 1972.

2. P. Stahl Skov & S. Norn: A simplified method for measuring basophil histamine release and blocking antibodies in hay fever patients. Basophil histamine content and cell preservation. Acta Allergol. 32: 170–182, 1977.

3. R. P. Siraganian: Automated histamine release. A method for in vitro allergy diagnosis. Int. Archs Allergy appl. Immun. 49: 108–110, 1975.

4. K. M. Taylor et al.: An enzymatic-isotopic microassay for measuring allergic release of histamine from blood and mast cells in vitro. Int. Archs Allergy appl. Immun. 61: 19–27, 1980.

5. P. Stahl Skov et al.: $^3$H-histamine release from human leucocytes. Allergy 34: 261–263, 1979.

What we claim is:

1. An analytical agent for use in the detection or determination of histamine in body fluids, which comprises individual glass microfibers fixed onto a carrier, said agent adapted for use in the detection or determination of histamine possibly released by allergic reaction in body fluids which further comprises the reversible deposition of at least one test allergen.

2. The analytical agent according to claim 1, wherein the individual glass microfibers are in the form of fine particles having dimensions ranging from 2 to 20 $\mu$m.

3. The analytical agent according to claim 1, wherein the individual glass microfibres used have the following typical oxide content: SiO$_2$ 57.9%, B$_2$O$_3$ 10.7%, Fe$_2$O$_3$ 5.9%, Al$_2$O$_3$ and Na$_2$O 10.1%, K$_2$O 2.9%, CaO 2.6% MgO 0.4%, BaO 5.0%, ZnO 3.9% and F 0.6%.

4. The analytical agent according to claim 1, wherein the carrier is selected from the group consisting of test tubes, glass plates and strips.

5. An analytical agent as in claim 1, adapted for use in the competitive detection or determination of histamine in body fluids additionally comprising labelled histamine.

6. An analytical agent as in claim 5, wherein the histamine is labelled with a radical selected from the group consisting of tritium, iodine-125, fluorescent molecules, bacteriophages, non-fluorescent enzymes, non-fluorescent coenzymes and non-fluorescent enzyme inhibitors.

7. A diagnostic test device comprising an analytical histamine binding agent prepared by crushing glass microfibers in aqueous suspension to form fine glass microfiber particles, selecting a predetermined amount of the resulting glass microfiber particles having dimensions ranging from 2 to 20 μm, and depositing and fixing the selected glass microfiber particles onto a carrier, said test device adapted for use in the detection or determination of histamine possibly released by allergic reaction in body fluids additionally comprising at least one test allergen reversibly deposited onto the carrier.

8. A diagnostic test device as in claim 7, wherein the glass microfibers are boron silicate fibers having the following typical oxide content: $SiO_2$ 57.9%, $B_2O_3$ 10.7%, $Fe_2O_3$ 5.9%, $Al_2O_3$ and $Na_2O$ 10.1%, $K_2O$ 2.9%, CaO 2.6% MgO 0.4%, BaO 5.0%, ZnO 3.9% and F 0.6%.

9. A diagnostic test device as in claim 7 wherein the carrier is selected from the group consisting of test tubes, glass plates and strips.

10. A diagnostic test device as in claim 7, adapted for use in the competitive detection or determination of histamine in body fluids additionally comprising labelled histamine.

11. A diagnostic test device as in claim 10, wherein the histamine is labeled with a radical selected from the group consisting of tritium, iodine-125, fluorescent molecules, bacteriophages, non-fluorescent enzymes, non-fluorescent coenzymes and non-fluorescent enzyme inhibitors.

12. A diagnostic test device comprising an analytical histamine binding agent prepared by crushing glass microfibers in aqueous suspension to form fine glass microfiber particles, selecting a predetermined amount of the resulting glass microfiber particles having dimensions ranging from 2 to 20 μm, and depositing and fixing the selected glass microfiber particles onto a carrier, said test device adapted for use in the direct detection or determination of histamine in body fluids additionally comprising coupling with a fluorophore compound.

13. A diagnostic test device as in claim 12, wherein the glass microfibers are boron silicate fibers having the following typical oxide content: $SiO_2$ 57.9%, $B_2O_3$ 10.7%, $Fe_2O_3$ 5.9%, $Al_2O_3$ and $Na_2O$ 10.1%, $K_2O$ 2.9%, CaO 2.6%, MgO 0.4%, BaO 5.0%, ZnO 3.9% and F 0.6%.

14. A diagnostic test device as in claim 12 wherein the carrier is selected from the group consisting of test tubes, glass plates and strips.

15. A diagnostic test device as in claim 12, adapted for use in the competitive detection or determination of histamine in body fluids additionally comprising labelled histamine.

16. A diagnostic device as in claim 15, wherein the histamine is labelled with a radical selected from the group consisting of tritium, iodine-125, fluorescent molecules, bacteriophages, non-fluorescent enzymes, non-fluorescent coenzymes and non-fluorescent enzyme inhibitors.

* * * * *